(12) United States Patent
Figallo et al.

(10) Patent No.: US 11,224,445 B2
(45) Date of Patent: Jan. 18, 2022

(54) APPARATUS AND KIT FOR MAKING HOLES AT CONTROLLED DEPTH AND OF DIFFERENT DIAMETERS ON CHONDRAL AND OSTEOCHONDRAL SURFACES

(71) Applicant: FIN-CERAMICA FAENZA S.P.A., Faenza (IT)

(72) Inventors: Elisa Figallo, Bologna (IT); Jordan N. Jacobs, Randolph, MA (US); Claudio De Luca, Faenza (IT)

(73) Assignee: FIN-CERAMICA FAENZA S.P.A., Faenza (IT)

( * ) Notice: Subject to any disclaimer, the term of this patent is extended or adjusted under 35 U.S.C. 154(b) by 183 days.

(21) Appl. No.: 16/335,259

(22) PCT Filed: Sep. 18, 2017

(86) PCT No.: PCT/IB2017/055626
§ 371 (c)(1),
(2) Date: Mar. 21, 2019

(87) PCT Pub. No.: WO2018/055501
PCT Pub. Date: Mar. 29, 2018

(65) Prior Publication Data
US 2019/0254683 A1    Aug. 22, 2019

(30) Foreign Application Priority Data
Sep. 21, 2016  (IT) .......................... 102016000094601

(51) Int. Cl.
*A61B 17/16* (2006.01)
*A61B 90/00* (2016.01)
(Continued)

(52) U.S. Cl.
CPC ...... *A61B 17/1626* (2013.01); *A61B 17/1633* (2013.01); *A61B 17/1637* (2013.01);
(Continued)

(58) Field of Classification Search
CPC ............................................. A61B 17/16–1697
See application file for complete search history.

(56) References Cited

U.S. PATENT DOCUMENTS

| | | | | |
|---|---|---|---|---|
| 4,798,213 A | * | 1/1989 | Doppelt | A61B 10/025 30/174 |
| 5,919,196 A | * | 7/1999 | Bobic | A61B 10/025 606/86 R |

(Continued)

FOREIGN PATENT DOCUMENTS

| | | |
|---|---|---|
| EP | 2138110 A2 | 12/2009 |
| EP | 2564792 A1 | 3/2013 |
| WO | 2013179013 A1 | 12/2013 |

OTHER PUBLICATIONS

Search Report and Written Opinion of PCT/IB2017/055626 dated Jan. 2, 2018.

*Primary Examiner* — Zade Coley
(74) *Attorney, Agent, or Firm* — Silvia Salvadori, P.C.; Silvia Salvadori

(57) ABSTRACT

An apparatus and kit for making holes of controlled depth and different diameters on chondral and osteochondral surfaces, comprises: a reamer member (2) having a cutting head (3) for removing tissue from said chondral and osteochondral surface (A), said member (2) being mobile approaching the chondral and osteochondral surface (A) for arranging the head (3) at said tissue; guide means (4) for guiding the reamer member (2) that can be firmly associated with the chondral or osteochondral surface (A), said reamer member (2) being slidable along said guide means (4); and mechanical means (5) for controlling the depth of the hole interposed between the reamer member (2) and the guide means (4) for defining an end stop of the reamer member (2) in the respective movement towards said chondral and osteochondral surface (A).

7 Claims, 5 Drawing Sheets

(51) Int. Cl.
 *A61B 17/17* (2006.01)
 *A61B 17/00* (2006.01)
(52) U.S. Cl.
 CPC ............ *A61B 90/03* (2016.02); *A61B 17/162* (2013.01); *A61B 17/1635* (2013.01); *A61B 17/1675* (2013.01); *A61B 17/1697* (2013.01); *A61B 17/1764* (2013.01); *A61B 2017/0046* (2013.01); *A61B 2017/1602* (2013.01); *A61B 2090/034* (2016.02)

(56) References Cited

U.S. PATENT DOCUMENTS

| | | | | |
|---|---|---|---|---|
| 6,488,033 B1* | 12/2002 | Cerundolo | ......... | A61B 17/1637 128/898 |
| 6,514,258 B1* | 2/2003 | Brown | .................. | A61C 1/084 408/202 |
| 7,488,327 B2* | 2/2009 | Rathbun | ............ | A61B 17/1728 606/96 |
| 7,866,979 B2* | 1/2011 | Verban, Jr. | ............. | A61C 1/084 433/75 |
| 8,221,423 B2* | 7/2012 | Gil | ..................... | A61B 17/1635 606/80 |
| 8,460,297 B2* | 6/2013 | Watlington | .......... | A61B 17/162 606/80 |
| 9,271,743 B2* | 3/2016 | Asfora | ................ | A61F 2/30988 |
| 2004/0034437 A1* | 2/2004 | Schmieding | ....... | A61B 17/1675 623/20.14 |
| 2006/0188840 A1* | 8/2006 | Verban, Jr. | ............. | A61C 1/084 433/75 |
| 2007/0191852 A1* | 8/2007 | Shimko | .............. | A61B 17/1604 606/79 |
| 2009/0209962 A1* | 8/2009 | Jamali | ................ | A61F 2/30756 606/81 |
| 2009/0299371 A1* | 12/2009 | Steiner | ............... | A61B 17/1675 606/79 |
| 2009/0299372 A1* | 12/2009 | Steiner | ............... | A61B 17/1675 606/79 |
| 2014/0142643 A1* | 5/2014 | Bake | ...................... | A61B 17/56 606/86 R |
| 2014/0243836 A1* | 8/2014 | Bake | ...................... | A61B 17/17 606/88 |
| 2015/0105696 A1* | 4/2015 | Litke | ...................... | A61B 5/742 600/587 |

* cited by examiner

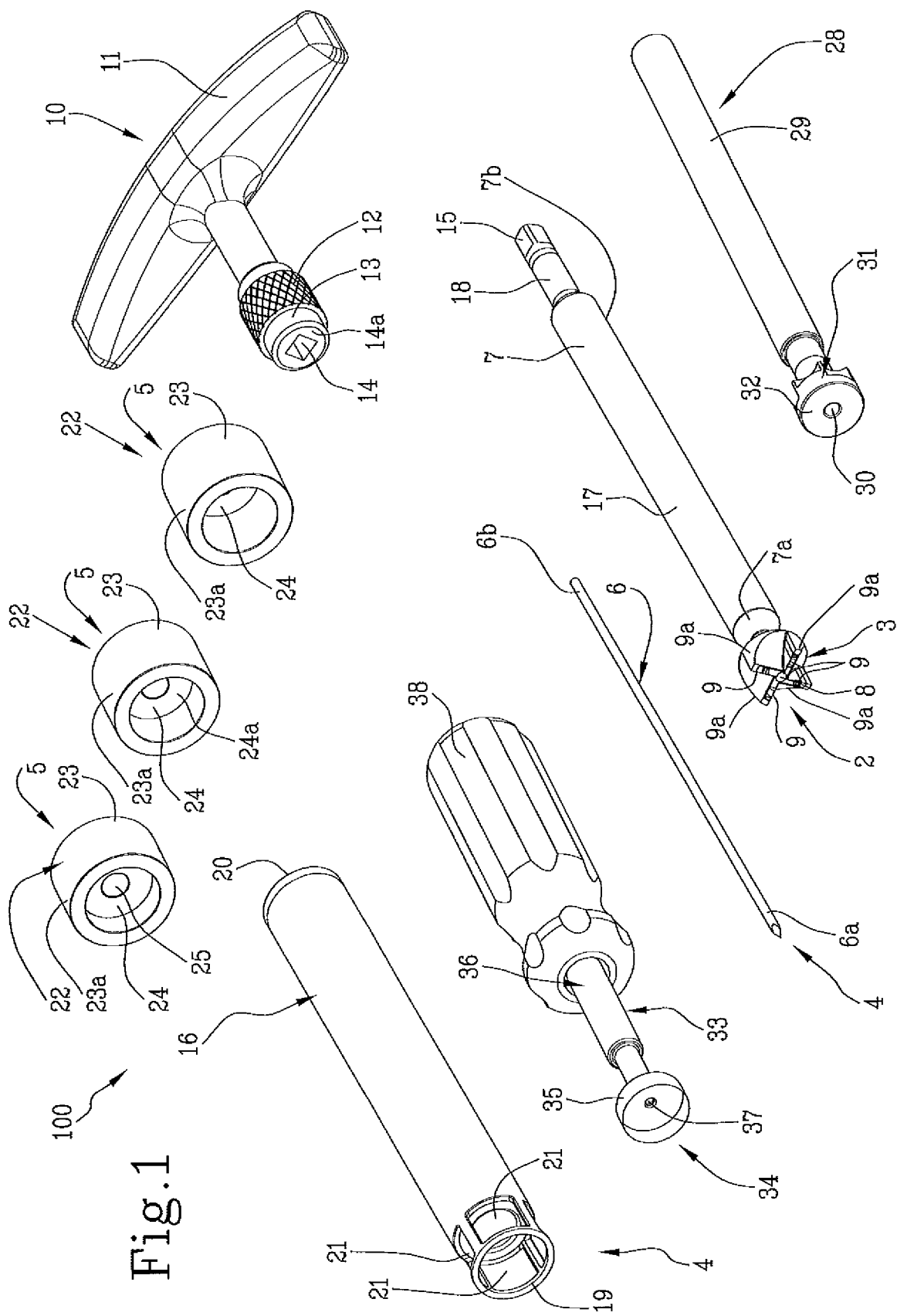

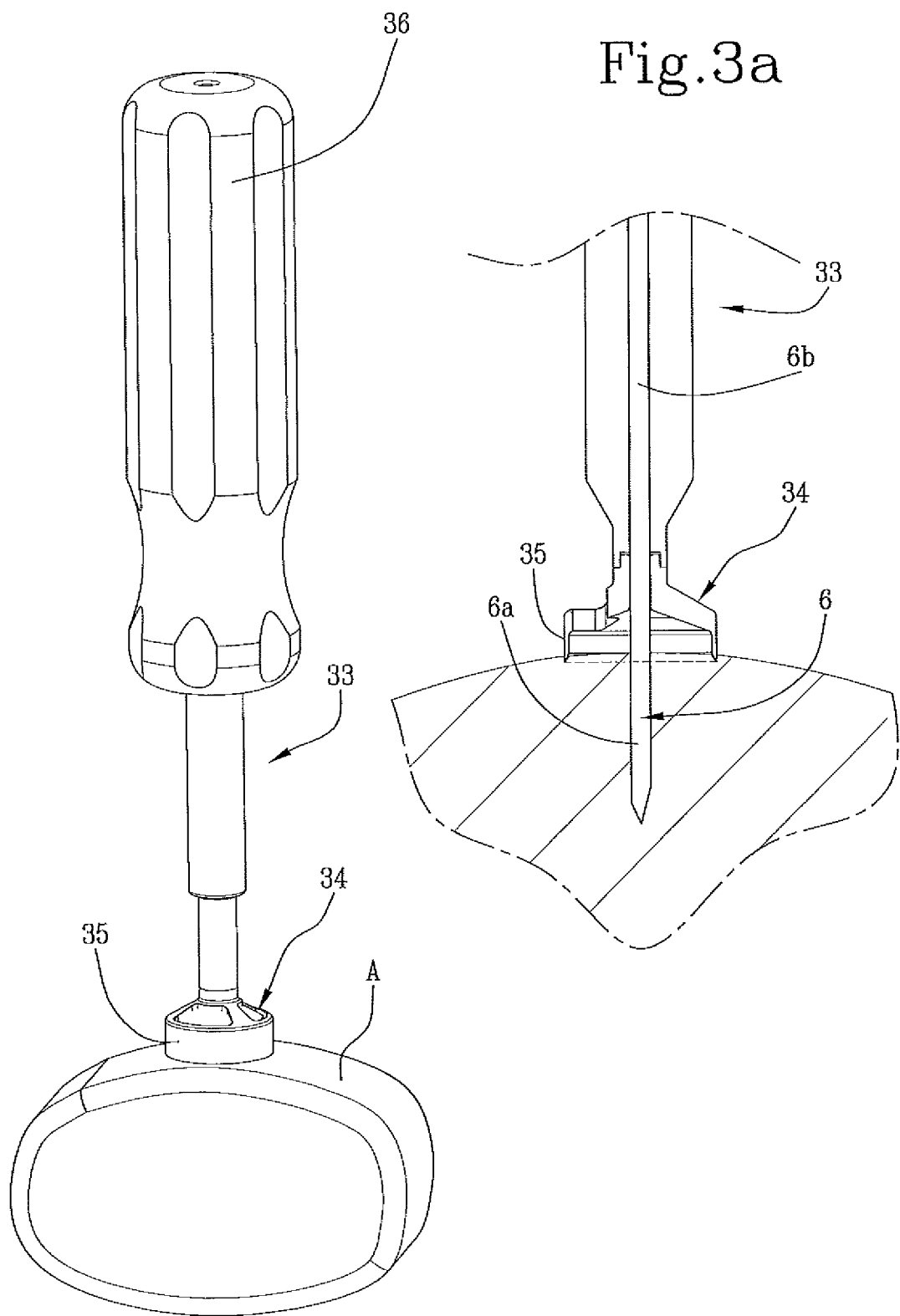

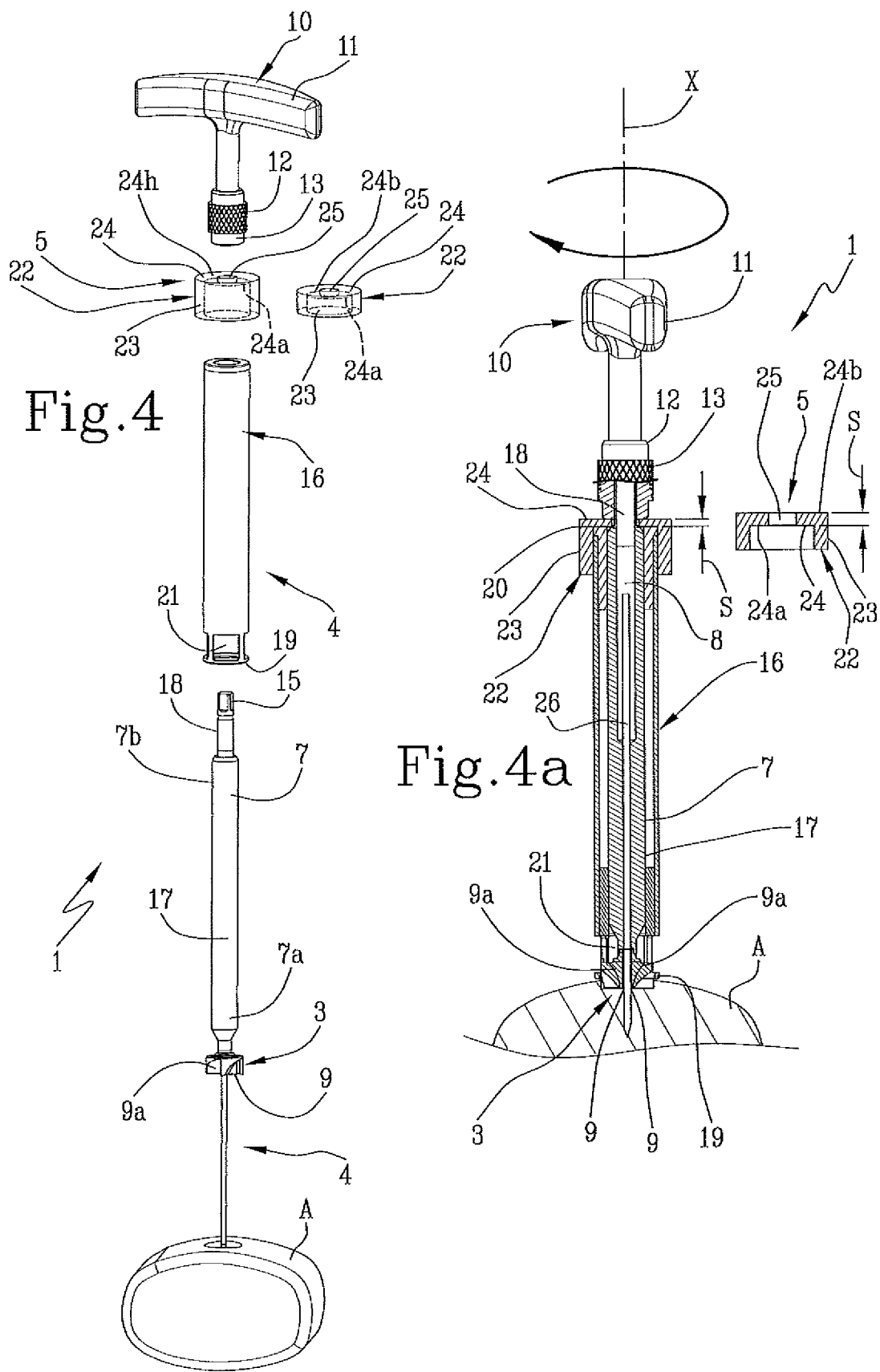

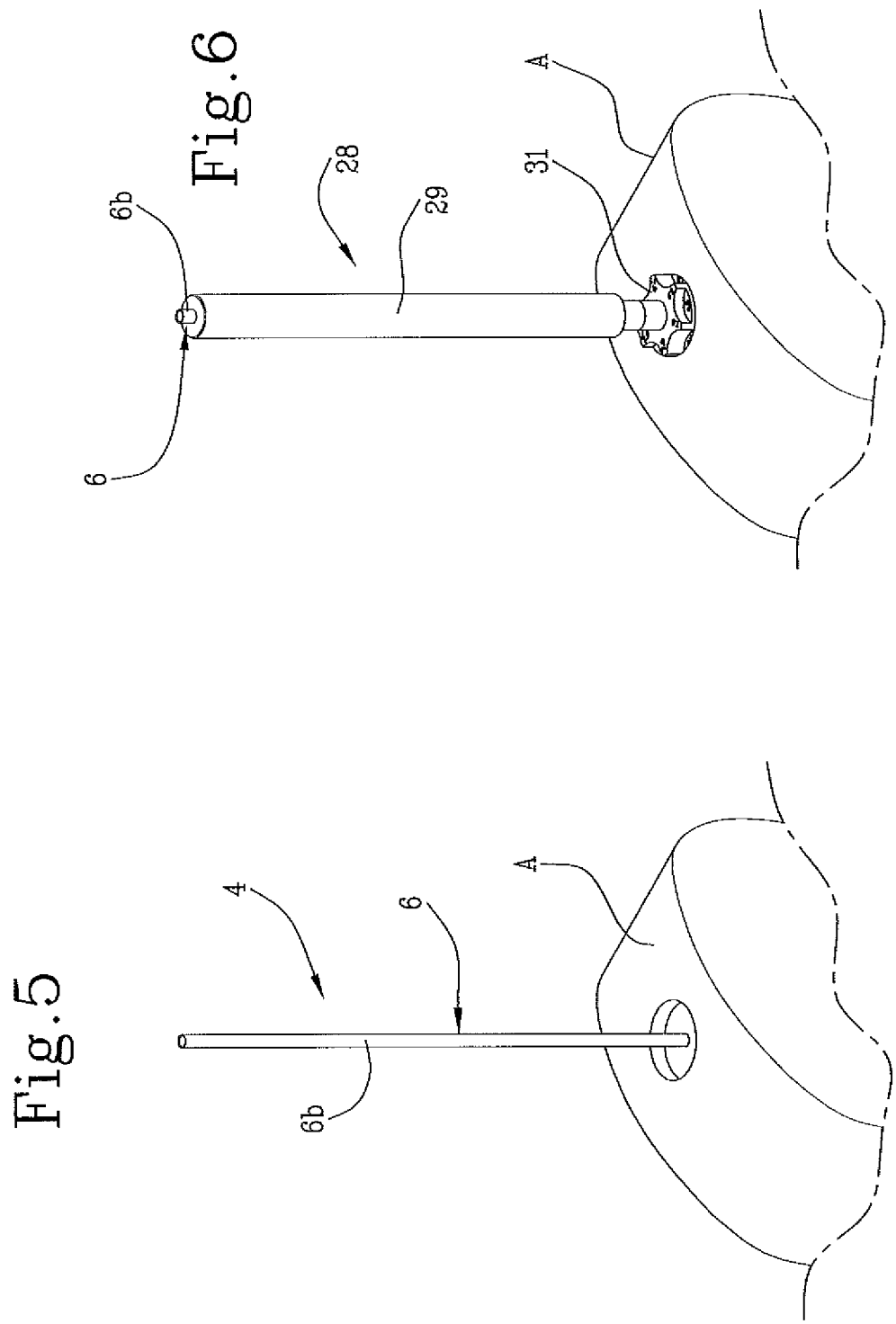

APPARATUS AND KIT FOR MAKING HOLES AT CONTROLLED DEPTH AND OF DIFFERENT DIAMETERS ON CHONDRAL AND OSTEOCHONDRAL SURFACES

This application is a U.S. national stage of PCT/IB32017/055626 filed on 18 Sep. 2017 which claims priority to and the benefit of Italian Application No. 102016000094601 filed on 21 Sep. 2016, the content of which are incorporated herein by reference in their entireties.

TECHNICAL FIELD

The present invention relates to an apparatus and a kit for making holes at controlled depth and of different diameters on chondral and osteochondral surfaces.

In particular, the present invention relates to an apparatus able to make holes for cartilaginous and osteocartilaginous substitutes for the regeneration of chondral and osteochondral tissues such as, for example, the cartilaginous and osteocartilaginous substitutes described in patent application no. WO2006092718 by the same Applicant.

The present invention further relates to a kit for preparing the damaged chondral or osteochondral area for the creation of the mentioned hole.

BACKGROUND OF THE INVENTION

As is known, chondral and osteochondral substitutes for the regeneration of the chondral and osteochondral tissues are applied for the treatment of lesions characterised by areas lacking (totally or partially) cartilaginous or osteocartilaginous tissue, or for the neo-formation of cartilaginous tissue and/or sub-chondral bone tissue.

Such chondral or osteochondral lesions can present in different forms, sizes and depths, according to the pathology or the cause of the damage, therefore surgical techniques vary according to these parameters and the substitute to be applied.

Before proceeding with the implant of the cartilaginous and osteocartilaginous substitutes, it is appropriate to expose the area of the lesion through an arthrotomic or mini-arthrotomic incision, in order to remove the damaged tissue. In order to guarantee better mechanical stability and better integration of the cartilaginous or osteocartilaginous substitute with the surrounding tissue and, therefore, better efficacy of the surgery, it is appropriate to prepare a suitable housing for the implant of cartilaginous or osteocartilaginous substitute, for example, with side walls perpendicular to the bottom of the lesion itself and with a flat bottom.

In order to proceed with the application of the chondral or osteochondral substitute the lesion should be, therefore, appropriately shaped and prepared, defining a suitable housing site.

For this purpose, a hole is prepared in correspondence of the lesion with a predetermined shape, width and depth, both based on the size of the lesion and according to the size of the respective chondral or osteochondral substitute to implant.

For making the hole, manually activated equipment is usually used, such as, for example, reamer members adapted to enlarge the lesion to a determined size. Such equipment comprises a cutting head adapted to remove chondral or osteochondral tissue from the area surrounding the lesion and thus to define the hole. In particular, the cutting head has an edge which, running along the surface, scrapes the surface itself removing surface tissue from it. The movement of the edge is performed manually by an operator who, by acting on a respective gripping member, compresses the head onto the surface and simultaneously rotates the head in order to remove the chondral or osteochondral tissue.

Generally, the head is supported by a containment body which is withheld manually during the compression and rotation action, to correctly position the head at the area to be bored.

The size of the hole is, therefore, determined by the size of the cutting head and edge. Therefore, according to the desired width, the apparatus with a suitably sized head is chosen.

Furthermore, the depth of the hole is adjusted by the compression action of the user pushing the head in a perpendicular direction to the planar extension of the surface.

Therefore, the control of the depth of the hole is performed manually by the operator who sees to stopping the scraping action once the determined depth has been reached.

However, this control is subject to a higher margin of error by the operator in the manual compression assessments. In this context it is worth noting that a hole that is excessively deep or shallow with respect to the envisaged one can lengthen the surgical procedure and have a negative effect on the clinical outcome of the operation.

Consequently, to facilitate control of the depth, optical measurement systems are envisaged, generally arranged on the containment body and comprising numerical references visible to the operator during their tissue removal action. However, such systems do not guarantee precise measurement of the depth, since the numerical references cannot be displayed during the boring action. In this situation, the operator must periodically stop the compression and rotation actions of the head to check the depth reached through the mentioned numerical references.

To overcome this drawback, equipment is provided with a determined axial sliding of the cutting head with respect to the containment body. In this case, the stroke of the head determines the depth to be reached in the material removal operations.

Therefore, the crushing action is prolonged by the operator until the head reaches its maximum limit of extension, therefore without the possibility to overdo the chondral or osteochondral tissue removal action.

However, even this solution is not exempt from a significant drawback, due to the need to provide an excessive amount of apparatus, each of which is used for making a hole of a predetermined size.

Consequently, the preparation of the hole is more costly precisely due to the need to have a very large set of apparatus, in which each apparatus is provided to make a hole with a corresponding depth.

In addition to this drawback, it should also be considered that to always guarantee the correct operation of the cutting head, the apparatus is subject to periodic maintenance operations that substantially affect the management costs of the apparatus, given the need to operate on a multitude of tools.

A further significant drawback of the known apparatus summarised above is determined by the difficulty for the operator to orient the head with respect to the chondral or osteochondral surface to be removed. In fact, it is worth noting that, as described above, the action of positioning and withholding the containment body with respect to the chondral and osteochondral surface is performed manually. Consequently, during the rotation of the head it is difficult to keep the edge with the respective advancement direction perpendicular to the planar extension of the chondral or osteochondral surface.

In this context, the main technical task of the present invention is to provide an apparatus and a kit for making holes on chondral and osteochondral surfaces that is able to overcome the drawbacks described above.

DESCRIPTION OF THE INVENTION

The apparatus and the kit according to the present invention have the aim of facilitating the implant of cartilaginous and osteocartilaginous substitutes through mini-arthrotomic or arthrotomic surgery for the treatment of medium/small defects. This guarantees a less invasive, faster, more linear surgical approach and with lower margins of error, as well as a better reproducibility and precision in surgeries. It is also considered that this could minimise the onset of adverse events that can arise following a more invasive surgical approach. The instruments according to the present invention will also be able to create holes of controlled depths and different diameters for the treatment of chondral and osteochondral lesions.

Advantageously, the apparatus is able to make holes for the housing of cartilaginous and osteocartilaginous substitutes such as, for example, those described and illustrated in patent application WO2006092718 by the Applicant. Within the scope of said technical task, an important object of the invention is to propose a single apparatus able to make a hole of any depth.

In particular, it is an object of the present invention to provide an apparatus able to limit the compression action of the user, in order to make a hole with a predetermined depth by the actual user.

A further object of the present invention is to provide an apparatus able to effectively make a hole on chondral and osteochondral surfaces, and at the same time structurally simple and easy to use.

Moreover, a further object of the present invention is to provide a kit that can prepare the chondral or osteochondral surface in order to correctly create the hole.

The set technical task and the specified aims are substantially attained by an apparatus and a kit for making holes on chondral or osteochondral surfaces in accordance with one or more of the accompanying claims.

By way of indicative and non-limitative example, below is a description of an apparatus and a kit for making holes on chondral or osteochondral surfaces, in accordance with the present invention, wherein:

FIG. 1 shows a perspective view of a kit for making holes on chondral or osteochondral surfaces in accordance with the present invention;

FIGS. 2, 2a and 3 show perspective views of respective phases of use of the kit for preparing the chondral or osteochondral surface to be treated;

FIG. 3a shows a sectional side view of a portion of the kit of FIG. 3 during the preparation step of the chondral or osteochondral surface to be treated;

FIG. 4 shows a perspective and exploded view of an apparatus according to the present invention which is part of the mentioned kit for making holes on the chondral or osteochondral surface;

FIG. 4a shows a raised side view of the apparatus of FIG. 4 in a respective operating condition; and FIGS. 5 and 6 show perspective views of respective phases of use of the kit for preparing the chondral or osteochondral surface treated.

Figure 2A:
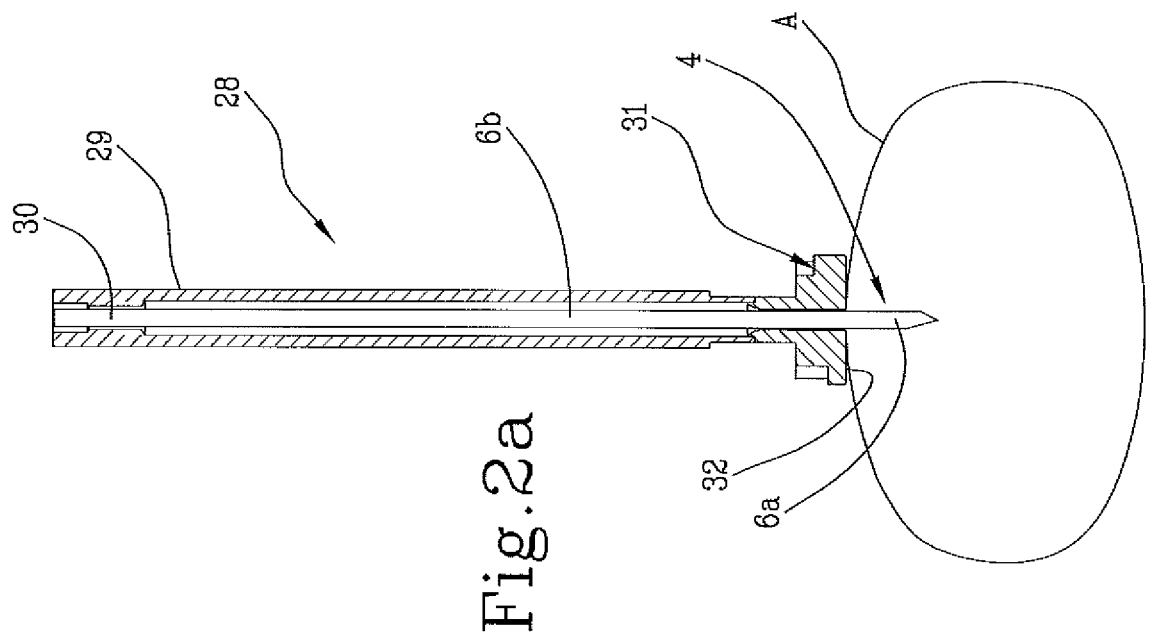

With reference to the appended figures, an apparatus for making holes on chondral or osteochondral surfaces "A" in accordance with the present invention is indicated overall with reference number 1 (FIGS. 4 and 4a). Apparatus 1 is comprised within a kit 100 illustrated overall in FIG. 1, provided to prepare and make the mentioned hole on surface "A".

In particular, with reference to FIGS. 1, 4 and 4a, apparatus 1 comprises a reamer member 2 having at least one cutting head 3 for removing tissue from the chondral or osteochondral surface "A" schematically illustrated solely by way of example in the form of a solid having a substantially oval conformation.

The reamer member 2 is mobile approaching the chondral or osteochondral surface, along an axis of longitudinal extension "X" for arranging the head 3 at the mentioned tissue.

The apparatus 1 further comprises guide means 4 of the reamer member 2 that can be firmly associated with the chondral or osteochondral surface A. In other words, during use, the guide means 4 are associated with the surface "A" to provide a stable reference for the head 3 during the respective removal operations of the chondral or osteochondral tissue.

In this situation, the reamer member 2 may be slidable along the mentioned guide means 4 and along the mentioned longitudinal axis "X".

The apparatus 1 further comprises mechanical control means 5 for controlling the depth of the hole interposed between the reamer member 2 and the guide means 4. The mechanical means 5 define a mechanical end stop of the reamer member 2 during the respective movement towards the chondral or osteochondral surface "A" and along the longitudinal axis "X".

Consequently, the depth of the hole, which depends on the movement of the reamer member 2 towards the surface "A" and along the axis "X", is determined mechanically by the mentioned means 5 which prevent, as will be better clarified below, the excessive sliding in depth of the head 3 on the chondral or osteochondral surface "A".

More particularly, the guide means 4 are constituted by at least one pin 6 having a rod-shaped conformation and partly insertable within the chondral or osteochondral surface "A".

In more detail, the pin 6 has an end tip 6a configured to penetrate into the surface "A" anchoring the pin 6 itself to the bone. In this situation, the pin 6 defines a free end 6b projecting from the surface "A" (FIG. 2a).

Preferably, the pin 6 is inserted at an area of the surface "A" in which there is a lesion to be treated through the application of a cartilaginous or osteocartilaginous substitute.

The free end 6b of the pin 6 is inserted into the reamer member 2 to allow the sliding of the member 2 itself along the extension of the pin 6 corresponding to the mentioned longitudinal axis "X".

With particular reference to FIGS. 1 and 4, it is to be noted that the reamer member 2 comprises a tubular element 7 having a hole 8 for housing the free end 6b of the pin 6.

The tubular element 7 has a circular cross section and defines a first end 7a on which the mentioned cutting head 3 is associated and equipped with the access opening to the hole 8 (FIG. 1).

It is to be noted on that point that the cutting head 3 comprises at least two edges 9 adapted to scrape the surface tissue to define the reaming action of the lesion.

Preferably, with reference to the appended figures, the cutting head 3 has four edges 9 in a "cross" arrangement, i.e. arranged on two perpendicular lines.

The edges 9 have an appropriately sized conformation according to the width of the hole to be obtained.

Again, it is worth noting that each edge 9 is afforded in a respective portion 9a projecting from the first end 7a of the tubular element 7. The portions 9a are reciprocally near and equally spaced so as to arrange the respective edges 9 at 90° from one another and with respect to the circumferential extension of the tubular element 7.

Consequently, the rotation of the tubular element 7 about the respective longitudinal axis "X" determines the rotation of the head 3 which makes the edges 9 creep along a circumferential path defining the circular surface of the hole to be made on the surface "A".

Again, the edges 9 may be equipped with relevant toothing promoting the scraping and removal action of the tissue. Preferably, such toothing is provided for large cutting heads 3. However, other outlines may be provided for appropriately preparing the head 3 for making holes on any type of surface, such as the bone surface.

The tubular element 7 further has a second end 7b opposite the first 7a and equipped with a gripping member 10 adapted to be held by the operator to transmit the rotation of the tubular element 7 (and therefore of the cutting head 3) about the axis "X" and simultaneously to press the head 3 against the surface "A".

Preferably, the gripping member 10 is removably associable with the tubular element 7 to be disengaged therefrom at the end of the reaming action.

In particular, the gripping member 10 has a first portion 11 defining an ergonomic handle, and a second portion 12 opposite the first 11, having a bushing 13 with a cylindrical conformation. The bushing 13 internally has a seat 14 (FIG. 1) for the jointing of the second end 7b of the tubular element 7.

In more detail, the seat 14 of the bushing has a square section conformation, for housing an end portion 15 of the second end 7b of the element 7, countershaped to the seat 14. In fact, it is worth noting that the terminal portion 15 has a square shaped cross section.

Advantageously, the terminal portion 15 is inserted into the seat 14 and engaged by mechanical jointing, in order to define the coupling of the gripping member 10 with the reamer member 2.

The apparatus 1 further comprises a support body 16 having a circular section tubular conformation for containing the reamer member 2.

In more detail, with particular reference to FIGS. 4 and 4a, the tubular element 7 has a first portion proximal to the first end 7a contained in the body 16, and a second portion 18 proximal to the second end 7b and projecting out of the support body 16.

As is more visible in FIGS. 1 and 4a, the body 16 has a first circular end edge 19 provided to be positioned on the chondral or osteochondral surface "A". Alternatively, the body 16 may have an edge 19 made by arched semi-parts spaced out from one another and extending along the same circular path.

Through windows 21 are further afforded at the edge 19 on the body 16, adapted to allow the visual control of the head 3 during the chondral or osteochondral tissue removal action.

In fact, it is worth noting that during the reaming operations, the edge 19 abuts against the surface "A" while the head 3 projects from the edge 19 for digging in depth. In this situation, optical control by the operator is required through the windows 21, for checking on the correct operation of the head 3.

On the opposite side of the first end edge 19, a second end edge 20 extends at the second portion 18 of the element 7.

Preferably, the internal cavity of the body 16 has a cross section with dimensions such as to allow the containment and sliding of the tubular element 7.

The mechanical means 5 for controlling the depth of the hole comprise at least one cylindrical insert 22 which can be fitted into the second portion 18 of the tubular element 7 so as to separate the bushing 13 of the gripping member 10 from the second end edge 20 of the support body 16.

Advantageously, the cylindrical insert 22 has a cup-shaped conformation defining a lateral wall 23 having a substantially annular profile, and a central wall 24 having a circular profile.

The central wall 24 has a through hole 25 for inserting the second portion 18 of the tubular element 7. Furthermore, the central wall 24 has a thickness "S" (FIG. 4a) defining the depth of the hole afforded on the chondral or osteochondral surface "A".

In other words, the central wall 24 spaces out the bushing 13 from the body 16 preventing the bushing 13 from coming into contact with the second edge 20 during the reaming action.

In fact, it is worth noting that the central wall 24 has an internal face 24a facing towards the support body 16 and that can be fitted onto the second end edge 20, and an external face 24b facing the bushing 13 and that can be fitted onto a flat surface 14a of the bushing 13 itself on which the mentioned jointing seat 14 is afforded.

Consequently, the thickness value "S" (distance between the internal face 24a and the external one 24b) of the central wall 24 is inversely proportional to the depth of the hole.

Again, the lateral wall 23 extends around the second end edge 20 of the support body 16.

The lateral wall 23 further has an external surface 23a showing the alphabetical/numerical/alpha-numerical references or other symbols and icons indicative of the depth of the hole to be made on the chondral or osteochondral surface "A" (and therefore the thickness value "S" of the central wall 24).

Such references therefore provide the operator with indications on the most suitable cylindrical insert 22 for making the hole.

For that purpose, the cylindrical insert 22 is removably associated with the second portion 18 of the tubular element 7 to be substituted with an insert 22 having a different thickness "S" and therefore able to provide a suitable mechanical end stroke for reaching the predetermined depth of the hole.

As illustrated in FIG. 4, the insert 22 is fitted onto the second portion 18 of the tubular element 7 until the internal face 24a is in abutment on the second end edge 20. Subsequently, the gripping member 10 is coupled to the tubular element 7 through the insertion of the terminal portion 15 into the seat 14.

In this way, by acting on the handle 11, the tubular element 7 is rotated and simultaneously pushed towards the surface "A" until the flat surface 14a of the bushing 13 is in abutment on the external face 24b of the central wall 24.

In any case, the presence of the insert 22 ensures the correct depth that the head 3 must reach in the operations for removing chondral or osteochondral tissue.

The present invention further relates to a kit 100 for making holes, which comprises the mentioned apparatus 1.

In particular, as shown in FIG. 1, the kit 100 has an element 28 for applying the pin 6, comprising a body 29 equipped with a through cavity 30 for inserting the pin 6.

The element 28 for applying the pin 6 has a flat end portion 31 of the body 29, equipped with an access hole to the through cavity 30 (FIG. 1).

In more detail, the flat portion 31 has a contact surface 32 with the chondral and osteochondral surface "A" lying on an extension plane perpendicular to the longitudinal extension axis of the body 29.

Advantageously, as shown in the sectional view of FIG. 2a, the orientation of the contact surface 32 with respect to the body 29 and the respective through cavity 30 allows the pin 6 to be arranged with the respective longitudinal axis perpendicular to the lying plane of the chondral or osteochondral surface "A".

Figure 2:
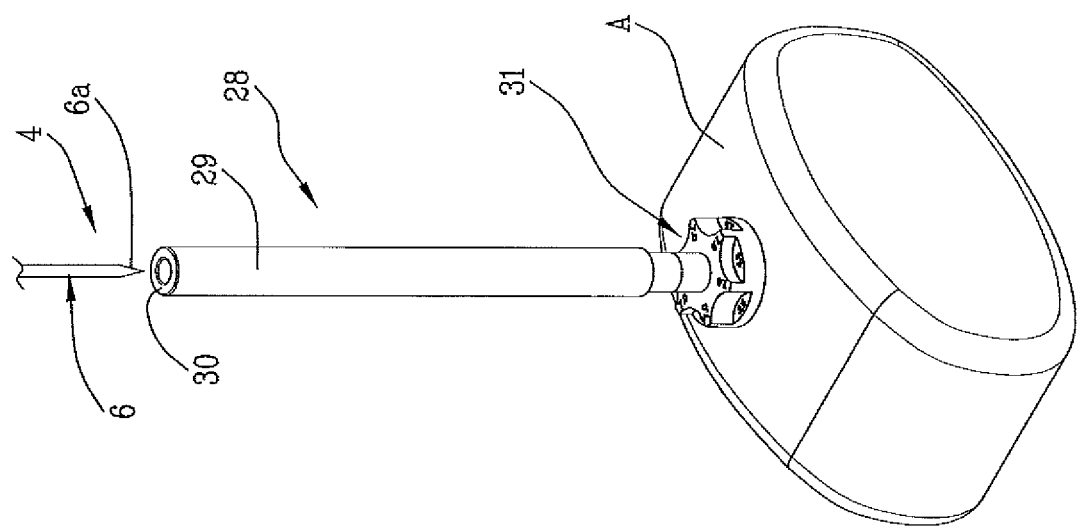

As shown in FIGS. 2 and 2a, the element 28 for applying the pin 6 rests on the surface "A" with the respective contact surface 32 fitted onto the lesion to be treated (not shown in the appended figures).

Once the contact surface 32 is resting on the chondral or osteochondral surface "A" the pin 6 is inserted into the through cavity 30 making the end 6a penetrate into the surface "A" (FIG. 2a). It is to be noted that the body 29 of the element 28 for applying the pin 6 has the same length of the free end 6b of the pin 6 inserted into the chondral or osteochondral surface "A".

Consequently, the optimal depth of insertion of the pin 6 is determined by inserting the pin 6 into the surface "A" until the respective free end 6b is fully contained within the cavity 30.

Once the pin 6 has been inserted, the body 29 is extracted leaving the pin 6 projecting from the area of the surface "A" for boring.

The kit 100 further comprises an incision member 33, having at least one cutting tool 34 for making an incision on the chondral or osteochondral reference surface "A" for positioning the head 3.

In particular, the cutting tool 34 comprises a circular blade 35 for defining an incision with a circular profile. The tool 34 is coupled to the end of a hollow body 36, having a substantially tubular conformation with a circular section.

The hollow body 36 has an internal hole 37 having access to the centre of the blade 35 and adapted to house the mentioned free end 6b of the pin 6.

The hollow body 2 is engaged with a gripping portion 38 that has an ergonomic handle, such as to allow the easy rotation of the tool 34 on the chondral or osteochondral surface. The gripping portion 38, which extends from the opposite side to the cutting tool 34, preferably has a substantially cylindrical conformation to be held by the operator and easily moved.

Also in this case, the cutting tool 34 may be chosen with a respective diameter according to the hole to be made.

In this way, once the element 28 for applying the pin 6 has been removed, the hollow body 36 is fitted onto the free end 6b of the pin 6 inserted into the chondral and osteochondral surface "A".

Through the manual and/or possibly automatic action by using appropriate motorised systems acting on the portion 38, the operator can, therefore, incise the surface "A" pressing the circular blade 35 onto the surface "A" and simultaneously rotating the tool 34 to ease the incision (FIGS. 3 and 3a).

Once the incision has been made, the member 33 is extracted from the pin 6 which still remains engaged with the surface "A".

At this point, the gripping member 10 is coupled to the terminal portion 15 of the tubular element 7.

In this situation, it is to be noted that the kit 100 comprises a plurality of cylindrical inserts 22 having different thicknesses "S" and therefore defining different depths of the hole. It is also to be noted that, as can be seen more clearly in FIG. 1 and in FIG. 4, the larger the thickness "S" of the central wall 24 of the insert 22 is (and therefore the lower the depth of the hole), the lower the longitudinal section width of the lateral wall 23 is.

By way of example, FIG. 1 illustrates three inserts 22 respectively defining a depth of the hole equal to 2 mm, a depth of the hole equal to 4 mm and one equal to 6 mm. The lateral wall 23 of the insert defining the 6 mm hole is wider than the lateral wall 23 of the insert defining the 4 mm hole. The lateral wall 23 of the insert defining the 4 mm hole is wider than the lateral wall 23 of the insert which defines the depth of 2 mm.

Advantageously, the operator chooses the right insert 22 for the depth to be obtained, either by reading the alphabetical/numerical/alpha-numerical or ornamental references marked on the lateral wall 23 (as for example in FIG. 1) or by comparing the width of the wall 23 with the thickness of the chondral or osteochondral substitute to be implanted.

Therefore, the choice of insert 22 is made very simply and immediately, even simply by direct comparison between the chondral or osteochondral substitute and the lateral wall 23 of the insert 22.

Once the suitable insert 22 for the depth of the hole to be obtained has been chosen, it is fitted onto the second portion 18 of the element 7 and withheld at the second portion 18 itself through the subsequent engagement of the gripping member 10 on the terminal portion 15.

At this point the tubular element 7 is fitted onto the pin 6 by inserting the free end 6b into the hole 8 and making the first end edge 19 coincide with the circular incision previously made by the incision member 33.

Once the apparatus 1 is positioned, the head 3 is rotated and pressed onto the surface "A" for removing the chondral or osteochondral material with the consequent definition of the hole. As specified above, the insert 22 determines a mechanical end stop which defines the depth of the hole. Therefore, when the bushing 13 is brought into contact with the insert 22, the reaming operation is stopped and the apparatus 1 is removed from the pin 6.

The element 28 guided by the pin 6 into the hole A is further used in order to measure the depth of the hole. For that purpose, alphabetical/numerical/alpha-numerical indicators or graphical representations are marked, preferably engraved on visible surfaces of the portion 31.

Such indicators help the operator practically and quickly measure the depth of the hole.

Once the correct hole size has been checked, the element 28 and pin 6 are removed from the hole itself through manual traction.

The present invention presents numerous advantages and reaches the objects set.

Above all, the apparatus 1 is able to create holes of any depth, making use of a mechanical control determined by the inserts 22 with differentiated sizes.

Advantageously, the apparatus 1 is very cost-efficient since only the insert 22 is substituted, suitable for the depth of the hole to be made, but maintaining all the mechanical members for making the hole.

A further advantage of the present invention is provided by the structural and operating simplicity of the apparatus 1 able to effectively make a hole by making use of both a mechanical and optical depth control system.

Furthermore, the kit 100 allows the surface "A" to be prepared in order to make the hole correctly. This advantage is given by the pin 6 and by the respective insertion system which guarantees the perpendicularity of the pin 6 with respect to the surface "A". Consequently, the pin determines a guide and positioning member of the apparatus 1 for the correct direction of the cutting head 3 during the reaming step.

The invention claimed is:

1. A kit for making holes of controlled depth and different diameters on chondral and osteochondral surfaces, said kit comprising:

an apparatus for making holes of controlled depth and different diameters on chondral and osteochondral surfaces, said apparatus comprising:

a reamer member having a cutting head for removing tissue from said chondral and osteochondral surface, said reamer member being mobile approaching the chondral and osteochondral surface for arranging the head at said tissue;

guide means for guiding the reamer member that can be firmly associated with the chondral or osteochondral surface, said guide means comprising a pin partially insertable in the chondral and osteochondral surface on which a hole is afforded and a support body having a tubular conformation and having a first end edge that can be fitted onto the chondral or osteochondral surface;

said reamer member comprising a tubular element having a hole for housing a free end of the pin, said tubular element sliding axially within the support body and along the longitudinal extension of the pin during the removal of the tissue from the chondral or osteochondral surface, said tubular element having a first end defining said cutting head and equipped with the access opening to said hole, and a second end opposite the first end having a gripping member for rotating in a manual or motorised way the tubular element and the cutting head defining the removal of tissue from the chondral and osteochondral surface; the tubular element also presenting a first portion proximal to said first end configured to be housed in said support body and a second portion proximal to said second end configured to project outside the support body;

the gripping member comprising a first portion defining a handle, and a second portion opposite the first having a bushing defining internally a seat for the jointing of the second end of the tubular element; and mechanical means for controlling the depth of the hole interposed between the reamer member and the guide means for defining an end stop of the reamer member in the respective movement towards said chondral and osteochondral surface, the mechanical means comprising a plurality of cylindrical inserts having different thicknesses of the respective central walls corresponding to different hole depths, each cylindrical insert can be fitted onto the second portion of the tubular element to separate the bushing of the gripping member from a second end edge of the support body opposite the first end edge;

the kit comprising an application element for applying the pin, having a body equipped with a through cavity for the hole of the pin; and an incision member, having at least one cutting tool for making an incision on the chondral or osteochondral reference surface for positioning the cutting head.

2. The kit according to claim 1, wherein said application element for applying the pin comprises a flat portion having a through hole for receiving the pin, said flat portion being arranged at an end of the hollow body.

3. The kit according to claim 2, wherein said flat portion has a contact surface with the chondral or osteochondral surface and wherein said body extends perpendicularly to the planar extension of said contact surface for arranging the pin with the respective longitudinal axis perpendicular to the lying plane of the chondral or osteochondral surface.

4. The kit according to claim 1, wherein said cutting tool comprises a circular blade for defining an incision having a circular profile, and wherein said incision member further comprises a hollow body for housing the free end of the pin, and associated with the circular blade.

5. The kit according to claim 1, wherein said cylindrical insert has a cup-shaped conformation defining a lateral wall having an annular profile and a central wall having a circular profile and defining a through hole for housing the second portion of the tubular element; said central wall having a thickness defining the depth of the hole afforded on the chondral or osteochondral surface; said central wall having an internal face facing the support body and that can be fitted onto the second end edge, and an external face facing the bushing and that can be fitted onto a flat surface of the bushing itself on which said jointing seat is afforded.

6. The kit according to claim 5, wherein said lateral wall extends around the second end edge of the support body and in that it further comprises alphabetical/numerical/alphanumerical references or other symbols marked on an external cylindrical surface of said lateral wall and each of which is representative of the depth of the hole.

7. The kit according to claim 6, wherein said cylindrical insert is removably associated with the second portion of the tubular element to be substituted with an insert having a different thickness of the central wall.

* * * * *